United States Patent [19]

Herd et al.

[11] Patent Number: 4,474,671
[45] Date of Patent: Oct. 2, 1984

[54] PRODUCTS OF REACTION OF ORGANIC DIAMINES, BORON COMPOUNDS AND ACYL SARCOSINES AND LUBRICANTS CONTAINING SAME

[75] Inventors: Richard S. Herd, Woodbury; Andrew G. Horodysky, Cherry Hill, both of N.J.

[73] Assignees: Mobil Oil Corporation, New York, N.Y.

[21] Appl. No.: 463,745

[22] Filed: Feb. 4, 1983

[51] Int. Cl.³ .................... C10M 1/54; C10M 5/28
[52] U.S. Cl. .................... 252/33.6; 252/49.6; 252/51.5 A; 252/389 R; 252/392; 252/400 R; 252/403

[58] Field of Search ............... 252/33.6, 51.5 A, 49.6, 252/389, 400, 392, 403

[56] References Cited

U.S. PATENT DOCUMENTS 3,027,405  3/1962  Spivack ........................... 252/33.6
3,156,653  11/1964  Foehr et al. ..................... 252/33.6

Primary Examiner—Jacqueline V. Howard
Attorney, Agent, or Firm—Alexander J. McKillop; Michael G. Gilman; Claude E. Setliff

[57] ABSTRACT

Nitrogen- and boron-containing products, and their use in lubricants, are disclosed. Particularly, selected diamines are reacted with boron compounds and sarcosines to give partially borated, partial sarcosine salts of the diamine.

25 Claims, No Drawings

PRODUCTS OF REACTION OF ORGANIC DIAMINES, BORON COMPOUNDS AND ACYL SARCOSINES AND LUBRICANTS CONTAINING SAME

BACKGROUND OF THE INVENTION

1. Field of the Invention

The invention relates to nitrogen- and boron-containing reaction products and to their use in lubricant compositions. More particularly, the reaction products are made by reacting an organic diamine with a boron compound and an acyl sarcosine.

2. Summary of Previous Disclosures

It is well known that under certain conditions metal parts being lubricated will rust. That is to say, when certain types of materials that are normally susceptible to deterioration by oxidation or by corrosion come into contact with various organic media, rust may form. Organic compositions in both the liquid and solid form can induce such corrosion or oxidation. For example, it is known that liquid hydrocarbons in the form of various fuel oils, such as petroleum distillate hydrocarbon fuels, lubricating oils, or greases therefrom, tend to accumulate considerable quantities of water when maintained for long periods of time in storage vessels; and when subsequently brought into contact with metal surfaces in their functional environments, deterioration of said surfaces as a result of rust and corrosion occurs. In addition, where such lubricating oils are incorporated into lubricants in the form of greases, similar deleterious results are encountered.

No art is known that teaches or suggests the reaction product of the present compositions or their use in lubricants. It is well known that amines and other nitrogen-containing compounds have been used as antioxidants. For example, N-phenylalpha-naphthylamine has been used alone and in combination with other materials as an antioxidant.

Many varied borated amides, borated alkanolamines, borated ureas, amine salts or boron acids, chlorinated amine-boron complexes and aromatic amine-boron mixtures have been used in the past in commercial lubricant and fuel applications as described in U.S. Pat. Nos. 3,449,362; 3,254,025; 2,999,064; 4,226,734; 3,076,835; 4,025,445; 3,014,870; 3,014,869 and 3,007,873. In fact, alkylamines, alkyldiamines and borated adducts of alkylamines and diamines have been used as friction reducing additives in lubricants as described in U.S. Pat. No. 4,328,113. Various amine salts have also been used as antirust additives, but the presence of the boron moieties provides an extra dimension of oxidative and high temperature stability and friction reducing properties that similar non-borated amine salts lack. The partially borated N-hydrocarbyl alkylenediamine-acyl sarcosine salts described herein provide advantages in antirust, friction-reduction, oxidative and high temperature stability performance properties unavailable in any of the prior art disclosures. The additive compositions, as well as the lubricant and fuel compositions made therefrom are believed to be novel, and are not believed to be described in any reference.

SUMMARY OF THE INVENTION

In accordance with the invention there are provided a product of reaction obtained by (1) reacting an N-hydrocarbyl hydrocarbylenediamine of the formula:

$$RNHR^1NHR^2$$

wherein R is a $C_6$ to $C_{20}$ hydrocarbyl group, $R^1$ is a $C_1$ to $C_3$ hydrocarbylene group and $R^2$ is a hydrogen or a $C_1$ to $C_6$ hydrocarbyl group with (2) a boron-containing compound and (3) an acyl sarcosine of the formula:

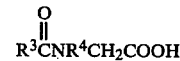

wherein $R^3$ is a $C_6$ to $C_{20}$ hydrocarbyl group and $R^4$ is a $C_1$ to $C_3$ hydrocarbylene group. Also provided are lubricant and liquid fuel compositions containing major proportions of lubricant or fuel and an antifriction or antirust amount of the product of this invention.

"Hydrocarbyl" and "hydrocarbylene" include saturated or unsaturated members. They may be alkyl or alkenyl, alkylene or alkenylene, aryl, aralkyl, alkaryl, where the aryl portion contains 6 to 14 carbon atoms, cycloalkyl or cycloalkenyl groups.

DESCRIPTION OF SPECIFIC EMBODIMENTS

Partially borated N-hydrocarbyl hydrocarbylenediamine-acyl sarcosine salts demonstrate antirust and friction-reducing properties when formulated into lubricants at low additive concentrations. These partially borated N-hydrocarbyl hydrocarbylenediamine-acyl sarcosine salts can be synthesized by the partial boration of N-hydrocarbyl alkylenediamines followed by reaction with and salt formation by the appropriate acyl sarcosine.

The diamines useful herein include N-octyl-1,3-propylenediamine, N-lauryl-1,3-propylenediamine, N-tetradecyl-1,3-propylenediamine, N-hexadecyl-1,3-propylenediamine, N-stearyl-1,3-propylenediamine, N-oleyl-1,3-propylenediamine, N-coco-1,3-propylenediamine, N-soya-1,3-propylenediamine, N-tallow-1,3-propylenediamine, N-hydrogenated tallow-1,3-propylenediamine and N-linoleyl-1,3-propylenediamine.

The boron compound can be any compound capable of boration. Preferred are boron oxide and a boron compound of the formula:

$$(R^5O)_xB(OH)_y$$

wherein $R^5$ is a $C_1$ to $C_6$ alkyl group, x is 0 to 3 and y is 0 to 3, the sum of x and y being 3. Included within the formula are boric acid and alkyl borates, such as the mono-, di- and trimethyl borates, the mono-, di- and triethyl borates, the mono-, di- and tributyl borates and the mono-, di- and trihexyl borates.

The acyl sarcosines, defined by:

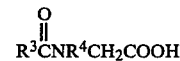

include, in addition to lauroyl sarocsine and cocoyl sarcosine of the Examples, oleoyl sarcosine, soyoyl sarcosine and tallowoyl sarcosine.

In carrying out the reaction, we generally first react the boron compound with the diamine in a manner to react from about 5% to about 95% of the available amine groups and then react at least 5% but up to 100%, of the remaining amine groups with the acyl sarcosine. Thus, there are present a significant portion of diamine molecules containing both boron and acyl sarcosinate moieties, which we believe leads to the exceptional properties of the products, i.e., their exceptional antirust, antifriction, antioxidant and high temperature stabilizing properties.

The reaction of the boron compound with the diamine is carried out at from about 80° C. to about 250° C., preferably about 120° C. to 180° C. Reaction of the product thus obtained is carried out at from about 30° C. to about 120° C.

Times of reaction are not critical. Thus, although we do not wish to be confined to any time limitation, we contemplate that the products of this invention can be made by carrying out the reaction for from 1 to 24 hours.

Solvents are preferred in carrying out the invention. Broadly, any solvent can be used that does not react, is a solvent for both the reactants and the reaction product and can be removed easily or is compatible with the environment in which the product will be used. We prefer the hydrocarbon solvents such as toluene, benzene and the xylenes.

The borated compounds disclosed herein are used with lubricants, including lubricating oils and greases therefrom, to the extent of from about 0.1% to about 10% by weight of the total composition, preferably from about 0.2% to about 2%. Furthermore, other additives, such as detergents, antioxidants, antiwear agents, viscosity index improvers, pour depressants, dispersants, and the like may be present. These can include phenates, sulfonates, succinimides, zinc dithiophosphates, polymers, calcium and magnesium salts and the like.

The lubricants contemplated for use with the esters herein disclosed include mineral and synthetic hydrocarbon oils of lubricating viscosity, mixtures of mineral oils and synthetic oils and greases from any of these, including mixtures. The synthetic hydrocarbon oils include long-chain alkanes such as cetanes and olefin polymers such as oligomers of hexene, octene, decene, and dodecene, etc. The products of the invention are especially effective in synthetic oils formulated using mixtures of synthetic hydrocarbom olefin oligomers and lesser amounts of hydrocarbyl carboxylate ester fluids. The other synthetic oils, which can be used alone with the borated compounds of this invention, or which can be mixed with a mineral or synthetic hydrocarbon oil, include (1) fully esterified ester oils, with no free hydroxyls, such as pentaerythritol esters of monocarboxylic acids having 2 to 20 carbon atoms, trimethylolpropane esters of monocarboxylic acids having 2 to 20 carbon atoms, (2) polyacetals and (3) siloxane fluids. Especially useful among the synthetic esters are those made from polycarboxylic acids and monohydric alcohols. More preferred are the ester fluids made by fully esterifying pentaerythritol, or mixtures thereof with di- and tripentaerythritol, with an aliphatic monocarboxylic acid containing from 1 to 20 carbon atoms, or mixtures of such acids.

A wide variety of thickening agents can be used in the greases of this invention. Included among the thickening agents are alkali and alkaline earth metal soaps of fatty acids and fatty materials having from about 12 to about 30 carbon atoms per molecule. The metals are typified by sodium, lithium, calcium and barium. Fatty materials are illustrated by stearic acid, hydroxylstearic acid, stearin, cottonseed oil acids, oleic acid, palmitic acid, myristic acid and hydrogenated fish oils.

Other thickening agents include salt and salt-soap complexes as calcium stearate-acetate (U.S. Pat. No. 2,197,263), barium stearate acetate (U.S. Pat. No. 2,564,561), calcium stearate-acetate (U.S. Pat. No. 2,999,066), and calcium salts and soaps of low-, intermediate- and high-molecular weight acids and of nut oil acids.

Another group of thickening agents comprises substituted ureas, phthalocyanines, indanthrene, pigments such as perylimides, pyromellitdiimides, and ammeline.

The preferred thickening gelling agents employed in the grease compositions are essentially hydrophobic clays. Such thickening agents can be prepared from clays which are initially hydrophilic in character, but which have been converted into a hydrophobic condition by the introduction of long chain hydrocarbon radicals into the surface of the clay particles. This is done to their use as a component of a grease composition, by, for example, subjecting them to a preliminary treatment with an organic cationic surface active agent, such as an onium compound. Typical onium compounds are tetraalkylammonium chlorides, such as dimethyl dioctadecyl ammonium chloride, dimethyl dibenzyl ammonium chloride and mixtures thereof. This method of conversion, being well known to those skilled in the art, is believed to require no further discussion, and does not form a part of the present invention.

More specifically, the clays which are useful as starting materials in forming the thickening agents to be employed in the grease compositions, can comprise the naturally occurring chemically unmodified clays. These clays are crystalline complex silicates, the exact composition of which is not subject to precise description, since they vary widely from one natural source to another. These clays can be described as complex inorganic silicates such as aluminum silicates, magnesium silicates, barium silicates, and the like, containing, in addition to the silicate lattice, varying amounts of cation-exchangeable groups such as sodium. Hydrophilic clays which are particularly useful for conversion to desired thickening agents include montmorillonite clays, such as bentonite, attapulgite, hectorite, illite, saponite, sepiolite, biotite, vermiculite, zeolite clays, and the like. The thickening agent is employed in an amount from about 0.5 to about 30, and preferably from 3 percent to 15 percent by weight of the total grease composition.

The liquid fuels contemplated include liquid hydrocarbon fuels such as fuel oils, diesel oils and gasolines and alcohol fuels such as methanol and ethanol or mixtures of these fuels. The additives are effective in the contemplated fuels to the extent of from about 20 to about 1500 pounds, preferably from about 30 to about 200 pounds thereof per 1000 barrels of fuel.

Having described the invention in general terms, the following are offered to specifically illustrate the development. It is to be understood they are illustrations only and that the invention shall not be limited except as limited by the appended claims.

EXAMPLE 1

N-Oleyl-1,3-Propylenediamine

N-Oleyl-1,3-propylenediamine (commercially available as Duomeen O from Armak Co.), had an iodine value of 60 min., 89% minimum apparent diamine activity, combining weight of approximately 180 and an amine value of approximately 312.

EXAMPLE 2

Partially Borated N-Oleyl-1,3-Propylenediamine

Approximately 267 g of N-oleyl-1,3-propylenediamine as described in Example 1, 35 g of toluene and 10 g of boric acid were charged to a 1 liter glass reactor fitted with an agitator, heater and Dean-Stark tube with condenser. The reactor contents were heated up to about 150° C., with agitation, using a slow nitrogen purge of the vapor space. The reactor contents were held at about 150° C. for 4½ hours until water evolution stopped. The solvent was removed by vacuum distillation and the partially borated diamine was filtered hot through diatomaceous earth. Substantially all of the boric acid appeared to have reacted and to have been incorporated into the intermediate partially borated diamine.

EXAMPLE 3

Partially Borated N-Oleyl-1,3-Propylenediamine-Partial Lauroyl Sarcosine Salt Approximately 29.6 g of partially borated N-oleyl-1,3-propylenediamine prepared as described in Example 2 and 11.2 g of lauroyl sarcosine were reacted, with agitation, for about ¾ hour at approximately 60° C. The product was somewhat waxy in nature and amber in color.

EXAMPLE 4

Partially Borated N-Oleyl-1,3-Propylenediamine-Partial Lauroyl Sarcosine Salt Approximately 26.7 g of partially borated N-oleyl-1,3-propylenediamine prepared as described in Example 2 and 15.1 g of lauroyl sarcosine were reacted, with agitation, for about ¾ hour at approximately 60° C. The product was amber colored and somewhat waxy in nature.

EXAMPLE 5

Partially Borated N-Oleyl-1,3-Propylenediamine-Partial Cocoyl Sarcosine Salt Approximately 29.6 g of partially borated N-oleyl-1,3-propylenediamine prepared as described in Example 2 and 5.6 g of cocoyl sarcosine were reacted, with agitation, for about ¾ hour at approximately 60° C. The product was amber colored and somewhat waxy in nature.

EXAMPLE 6

Partially Borated N-Oleyl-1,3-Propylenediamine-Partial Cocoyl Sarcosine Salt Approximately 26.7 g of partially borated N-oleyl-1,3-propylenediamine prepared as described in Example 2 and 10.1 g of cocoyl sarcosine were reacted, with agitation, for about ¾ hour at approximately 60° C. The product was amber colored and somewhat waxy in nature.

EVALUATION OF PRODUCTS

The products of the examples were formulated at the 2% wt. level into a fully formulated lithium soap grease without any other added antirust additive. The grease vehicle was a solvent naphthenic neutral mineral lubricating oil. The grease was then evaluated for antirust properties using an extremely severe rust test performed with 5% synthetic sea water in accordance with ASTM D-1743.

Table 1 summarizes the data obtained.

TABLE 1

| Evaluation of Antirust Properties | | |
| --- | --- | --- |
| | Concentration of Additive, Wt. % | Rust Test Results |
| Base Grease (lithium soap grease) | — | 3-10%, 3-15% |
| Example 1 | 2 | 3-2%, 3-5% |
| Example 2 | 2 | 3-2%, 3-10% |
| Example 3 | 2 | 2+, 2+ |
| Example 4 | 2 | 2, 2+ |
| Example 5 | 2 | 3-1%, 3-5% |
| Example 6 | 2 | 3-1%, 3-5% |

A bearing cup raceway showing no corrosion is rated 1. No more than three spots of a size just sufficient to be visible to the naked eye is rated 2. More than three spots but less than 1% of the surface area is rated 2+. One percent or more of the surface area is rated 3. (NOTE: the approximate percentage of surface area corrosion is shown with a 3 rating.) The antirust test results clearly show the antirust properties of these compositions.

Low Velocity Friction Apparatus

Description

The Low Velocity Friction Apparatus (LVFA) is used to measure the friction of test lubricants under various loads, temperatures, and sliding speeds. The LVFA consists of a flat SAE 1020 steel surface (diameter 1.5 in.) which is attached to a drive shaft and rotated over a stationary, raised, narrow ringed SAE 1020 steel surface (area 0.08 in.$^2$). Both surfaces are submerged in the test lubricant. Friction between the steel surfaces is measured as a function of the sliding speed at a lubricant temperature of 250° F. The friction between the rubbing surfaces is measured using a torque arm-strain gauge system. The strain gauge output, which is calibrated to be equal to the coefficient of friction, is fed to the Y axis of an X-Y-axis. To minimize external friction, the piston is supported by an air bearing. The normal force loading the rubbing surfaces is regulated by air pressure on the bottom of the piston. The drive system consists of an infinitely variable-speed hydraulic transmission driven by a ½ HP electric motor. To vary the sliding speed, the output speed of the transmission is regulated by a lever-cam motor arrangement.

Procedure

The rubbing surfaces and 12-13 ml of test lubricant are placed on the LVFA. A 240 psi load is applied, and the sliding speed is maintained at 40 fpm at ambient temperature for a few minutes. A plot of coefficients of friction ($U_k$) over the range of sliding speeds, 5 to 40 fpm (25-195 rpm), is obtained. A minimum of three measurements is obtained for each test lubricant. Then, the test lubricant and specimens are heated to 250° F., another set of measurements is obtained, and the system is run for 50 minutes at 250° F., 240 psi and 40 fpm sliding speed. Afterward, measurements of $U_k$ vs. speed are taken at 240, 400, 400 and 500 psi. Freshly polished steel specimens are used for each run. The surface of the steel is parallel ground to 4-8 microinches.

The data obtained are shown in Table 2. The data in Table 1 are reported as percent reduction in coefficient of friction at two speeds. The base 5W-30 synthetic lubricating oil was fully formulated, containing other additives, i.e., the detergent/dispersant/inhibition performance package. It had the following general characteristics:

| Viscosity 100° C. | 6.8 cs |
|---|---|
| Viscosity 40° C. | 36.9 cs |
| Viscosity Index | 143 |

TABLE 2

| Additive and Medium | Additive Conc. Wt. % | Reduction or % Change in Coefficient of Friction | |
|---|---|---|---|
| | | 5 Ft./Min. | 30 Ft./Min. |
| Base Oil | — | 0 | 0 |
| Example 1 | 4 | 20 | 15 |
| Example 5 | 1.0 | 20 | 17 |

The frictional test results clearly show the friction reducing properties of the partially borated alkyldiamine-acyl sarcosine product when compared to the base oil, even when compared to Example 1 containing four times the concentration of Example 5. Partially borated N-oleyl-1,3-propylenediamine-oleyl sarcosine salt is expected to demonstrate even more exceptional friction properties.

What is claimed is:

1. A product of reaction obtained by reacting (1) a N-hydrocarbyl hydrocarbylenediamine of the formula

RNHR$^1$NHR$^2$ wherein R is a $C_6$ to $C_{20}$ hydrocarbyl group, R$^1$ is a $C_1$ to $C_3$ hydrocarbylene group and R$^2$ is hydrogen or a $C_1$ to $C_6$ hydrocarbyl group with (2) a boron-containing compound at from about 80° C. to about 250° C. and (3) an acyl sarcosine of the formula $$R^3\overset{O}{\underset{\|}{C}}NR^4CH_2COOH$$

wherein R$^3$ is a $C_6$ to $C_{20}$ hydrocarbyl group and R$^4$ is hydrogen or a $C_1$ to $C_6$ hydrocarbyl group at from about 30° C. to about 120° C. and wherein in the reaction with the boron compound from about 5% to about 95% of the amine groups are reacted and in the reaction with the acyl sarcosine from about 5% to about 100% of the remaining amine groups are reacted.

2. The product of claim 1 wherein the hydrocarbyl groups are selected from the group consisting of from alkyl, alkenyl, aryl, aralkyl, alkaryl and cycloalkyl groups.

3. The product of claim 1 wherein the hydrocarbylene groups are alkylene or alkenylene groups.

4. The product of claim 1 wherein the diamines are selected from the group consisting of from N-octyl-1,3-propylenediamine, N-lauryl-1,3-propylenediamine, N-tetradecyl-1,3-propylenediamine, N-hexadecyl-1,3-propylenediamine, N-stearyl-1,3-propylenediamine, N-oleyl-1,3-propylenediamine, N-coco-1,3-propylenediamine, N-soya-1,3-propylenediamine, N-tallow-1,3-propylenediamine, N-hydrogenated tallow-1,3-propylenediamine and N-linoleyl-1,3-propylenediamine.

5. The product of claim 1 wherein the boron compound is boric oxide or one of the formula $(R^5O)_xB(OH)_y$ wherein R$^5$ is an alkyl group, x is 0 to 3 and y is 0 to 3, the sum of x and y being 3.

6. The product of claim 5 wherein the boron compound is boric acid or an alkyl borate.

7. The product of claim 6 wherein the boron compound is boric acid.

8. The product of claim 1 wherein the acyl sarcosine is the lauroyl, cocoyl, oleoyl, soyoyl or tallowoyl sarcosine.

9. The product of claim 8 wherein the amine is oleyl-1,3-propylenediamine, the boron compound is boric acid and the acyl sarcosine is lauroyl sarcosine.

10. The product of claim 8 wherein the amine is oleyl-1,3-propylenediamine, the boron compound is boric acid and the acyl sarcosine is cocoyl sarcosine.

11. A lubricant composition comprising a major proportion of a lubricating oil or grease therefrom and an antifriction amount of a product of reaction obtained by reacting (1) a N-hydrocarbyl hydrocarbylenediamine of the formula

RNHR$^1$NHR$^2$ wherein R is a $C_6$ to $C_{20}$ hydrocarbyl group, R$^1$ is a $C_1$ to $C_3$ hydrocarbylene group and R$^2$ is hydrogen or a $C_1$ to $C_6$ hydrocarbyl group with (2) a boron-containing compound at from about 80° C. to about 250° C. and (3) an acyl sarcosine of the formula $$R^3\overset{O}{\underset{\|}{C}}NR^4CH_2COOH$$

wherein R$^3$ is a $C_6$ to $C_{20}$ hydrocarbyl group and R$^4$ is hydrogen or a $C_1$ to $C_6$ hydrocarbyl group at from about 30° C. to about 120° C. and wherein in the reaction with the boron compound from about 5% to about 9% of the amine groups are reacted and in the reaction with the acyl sarcosine from about 5% to about 100% of the remaining amine groups are reacted.

12. The composition of claim 11 wherein the hydrocarbyl groups are selected from the group consisting of from alkyl, alkenyl, aryl, aralkyl, alkaryl and cycloalkyl groups.

13. The composition of claim 11 wherein the hydrocarbylene groups are alkylene or alkenylene groups.

14. The composition of claim 11 wherein the diamines are selected from the group consisting of from N-octyl-1,3-propylenediamine, N-lauryl-1,3-propylenediamine, N-tetradecyl-1,3-propylenediamine, N-hexadecyl-1,3-propylenediamine, N-stearyl-1,3-propylenediamine, N-oleyl-1,3-propylenediamine, N-coco-1,3-propylenediamine, N-soya-1,3-propylenediamine, N-tallow-1,3-popylenediamine, N-hydrogenated tallow-1,3-propylenediamine and N-linoleyl-1,3-propylenediamine.

15. The composition of claim 11 wherein the boron compound is boric oxide or one of the formula $(R^5O)_xB(OH)_y$ wherein R$^5$ is an alkyl group, x is 0 to 3 and y is 0 to 3, the sum of x and y being 3.

16. The composition of claim 15 wherein the boron compound is boric acid or an alkyl borate.

17. The composition of claim 16 wherein the boron compound is boric acid.

18. The composition of claim 11 wherein the acyl sarcosine is the lauroyl, cocoyl, oleoyl, soyoyl or tallowoyl sarcosine.

19. The composition of claim 18 wherein the amine is oleyl-1,3-propylenediamine, the boron compound is boric acid and the acyl sarcosine is lauroyl sarcosine.

20. The composition of claim 18 wherein the amine is oleyl-1,3-propylenediamine, the boron compound is boric acid and the acyl sarcosine is cocoyl sarcosine.

21. The composition of claim 11 wherein the lubricant is a lubricating oil or a grease therefrom.

22. The composition of claim 21 wherein the lubricating oil is (1) a mineral oil, (2) a synthetic oil or mixture of synthetic oils or (3) a mixture of (1) and (2).

23. The composition of claim 22 wherein the lubricant is a grease.

24. The composition of claim 22 wherein the lubricating oil is a synthetic oil or a mixture of synthetic oil.

25. The composition of claim 11 containing additionally, one or more, of phenates, sulfonates, succinimides, zinc dithiophosphates, polymers, calcium and magnesium salts.

* * * * *